US009965858B2

United States Patent
Wang

(10) Patent No.: US 9,965,858 B2
(45) Date of Patent: May 8, 2018

(54) IMAGE ALIGNMENT DEVICE, METHOD, AND PROGRAM, AND METHOD FOR GENERATING 3-D DEFORMATION MODEL

(71) Applicant: FUJIFILM Corporation, Tokyo (JP)

(72) Inventor: Caihua Wang, Tokyo (JP)

(73) Assignee: FUJIFILM CORPORATION, Tokyo (JP)

( * ) Notice: Subject to any disclaimer, the term of this patent is extended or adjusted under 35 U.S.C. 154(b) by 97 days.

(21) Appl. No.: 15/080,009

(22) Filed: Mar. 24, 2016

(65) Prior Publication Data

US 2016/0203609 A1    Jul. 14, 2016

Related U.S. Application Data

(63) Continuation of application No. PCT/JP2014/004867, filed on Sep. 24, 2014.

(30) Foreign Application Priority Data

Sep. 27, 2013   (JP) .................................. 2013-200806

(51) Int. Cl.
  *G06K 9/00*        (2006.01)
  *G06T 7/00*        (2017.01)
  (Continued)

(52) U.S. Cl.
  CPC ............ G06T 7/0032 (2013.01); A61B 5/055 (2013.01); A61B 5/1128 (2013.01);
  (Continued)

(58) Field of Classification Search
  None
  See application file for complete search history.

(56) References Cited

U.S. PATENT DOCUMENTS 7,117,026 B2 * 10/2006  Shao ........................ G06T 7/20
                                                   600/411
8,184,129 B2 *  5/2012  Shekhar ................ G01T 1/1611
                                                   345/648

(Continued)

FOREIGN PATENT DOCUMENTS

JP      2002-324238 A   11/2002
JP      2005-528974 A    9/2005
JP      2009-522005 A    6/2009

OTHER PUBLICATIONS

Mattes et al., "PET-CT image registratin in the chest using free-form deformations", IEEE Transactions on Medical Imaging, vol. 22, No. 1, Jan. 2003.*

(Continued)

*Primary Examiner* — Soo Park
(74) *Attorney, Agent, or Firm* — McGinn I.P. Law Group, PLLC.

(57) ABSTRACT

A first 3D image and a second 3D image imaged a target organ in different phases of respiration are acquired. A 3D deformation model of the target organ which is stored in advance and represents nonlinear 3D deformation of the target organ due to respiration, and which has been generated based on information about movement of the target organ due to respiration of plural patients, is read. The positions of pixels on the second 3D image representing the same positions on the target organ as plural sampled pixels in a target organ region on the first 3D image are estimated using displacement due to changes in phase of points on the 3D deformation model corresponding to the positions on the target organ represented by the pixels. Non-rigid alignment is performed between the first 3D image and the second 3D image using the estimated positions of the pixels.

13 Claims, 2 Drawing Sheets

(51) Int. Cl.
    A61B 8/00      (2006.01)
    A61B 5/055     (2006.01)
    A61B 6/00      (2006.01)
    A61B 5/11      (2006.01)
    A61B 5/113     (2006.01)
    A61B 6/03      (2006.01)
    A61B 5/00      (2006.01)
(52) U.S. Cl.
    CPC .......... *A61B 5/1135* (2013.01); *A61B 6/5235* (2013.01); *A61B 6/5288* (2013.01); *A61B 8/00* (2013.01); *G06T 7/003* (2013.01); *G06T 7/0046* (2013.01); *A61B 5/004* (2013.01); *A61B 6/032* (2013.01); *G06T 2200/04* (2013.01); *G06T 2200/08* (2013.01); *G06T 2207/10072* (2013.01); *G06T 2207/10081* (2013.01); *G06T 2207/10088* (2013.01); *G06T 2207/20221* (2013.01); *G06T 2207/30048* (2013.01); *G06T 2207/30061* (2013.01)

(56) References Cited

U.S. PATENT DOCUMENTS

| | | | | |
|---|---|---|---|---|
| 8,433,159 B1 * | 4/2013 | Nord | ....................... | G06T 7/269 375/240.16 |
| 8,620,055 B2 * | 12/2013 | Barratt | ................... | G06T 7/344 378/21 |
| 9,474,914 B2 * | 10/2016 | Thomson | ............... | A61B 6/032 |
| 9,582,906 B2 * | 2/2017 | Ra | ......................... | G06T 11/005 |
| 2003/0016853 A1 | 1/2003 | Oosawa | | |
| 2003/0233039 A1 * | 12/2003 | Shao | ........................ | G06T 7/20 600/407 |
| 2007/0160276 A1 | 7/2007 | Chen et al. | | |
| 2007/0237372 A1 | 10/2007 | Chen et al. | | |
| 2008/0205719 A1 * | 8/2008 | Pekar | .................... | G06T 3/0081 382/128 |
| 2012/0253170 A1 * | 10/2012 | Kim | ...................... | A61B 34/10 600/410 |

OTHER PUBLICATIONS

Reyes et al., "Model-based respiratory motion compensation for emissoin tomography image reconstruction", Physics in Medicine and Biology, 52 (2007) 3579-3600.*

International Search Report (ISR) (PCT Form PCT/ISA/210), in PCT/JP2014/004867, dated Jan. 20, 2015.

David Mattes; David R. Haynor; Hubert Vesselle; Thomas K. Lewellyn; William Eubank, "Nonrigid multimodality image registration", Proc. SPIE 4322, Medical Imaging 2001: Image Processing, pp. 1609-1620.

International Search Opinion (PCT/ISA/237) in PCT/JP2014/004867 dated Jan. 20, 2015, and a partial English translation thereof.

Japanese Office Action dated Nov. 8, 2016 with an English translation thereof.

* cited by examiner

IMAGE ALIGNMENT DEVICE, METHOD, AND PROGRAM, AND METHOD FOR GENERATING 3-D DEFORMATION MODEL

CROSS-REFERENCE TO RELATED APPLICATIONS

This application is a Continuation of PCT International Application No. PCT/JP2014/004867 filed on Sep. 24, 2014, which claims priority under 35 U.S.C. § 119(a) to Japanese Patent Application No. 2013-200806 filed on Sep. 27, 2013. Each of the above applications is hereby expressly incorporated by reference, in its entirety, into the present application.

BACKGROUND OF THE INVENTION

1. Field of the Invention

The present invention relates to an image alignment device, method, and program which perform alignment between two 3D images obtained by imaging a target organ of a patient in different phases of respiration, and to a method of generating a 3D deformation model for use in alignment.

2. Description of the Related Art

In image diagnosis using two 3D images acquired by imaging an object at different viewpoints using the same imaging device or different imaging devices, a non-rigid registration technique in which a transformation function (B-spline transformation function or the like) which matches the spatial positions of the object in both images with each other is estimated when both images are superimposed and one or both of the images are deformed using the estimated transformation function to align the two images is known.

David Mattes; David R. Haynor; Hubert Vesselle; Thomas K. Lewellyn; William Eubank, "Non-rigid multimodality image registration", Proc. SPIE 4322, Medical Imaging 2001: Image Processing, pp. 1609-1620 suggests a method which sets a plurality of control points at predetermined intervals inside an image space, determines the amount of displacement of the control points with the largest similarity between one image and another image deformed by displacing the positions of the control points using a quasi-Newton method, in particular, a limited memory Broyden Fletcher Goldfarb Shanno with boundaries (L-BFGS-B) method, and estimates a B-spline transformation function based on the amount of displacement of the control points at this time. According to this method, it is possible to perform very close local alignment on the two images with a comparatively small shift of the whole images.

JP2002-324238A discloses a method which, in alignment of two images with a comparatively large shift of the whole images, performs a linear transformation process (affine transformation or the like) of parallel movement, rotation, or enlargement and reduction on one image prior to close local alignment and performs rough alignment of the whole images in advance, thereby improving the accuracy of the local alignment.

SUMMARY OF THE INVENTION

However, according to the method described in JP2002-324238A in which a linear transformation process, such as affine transformation, is performed as rough alignment prior to close local alignment, in alignment between images of an organ, such as a lung, indicating nonlinear deformation as an object, there is a problem in that, even if rough alignment is performed prior to close local alignment, a region where rough alignment cannot be performed with sufficient accuracy such that subsequent close local alignment can be appropriately performed partially occurs.

The invention has been accomplished in consideration of the above-described situation, and an object of the invention is to provide an image alignment device, method, and program capable of performing more accurate alignment between two 3D images obtained by imaging a target organ of a patient in different phases of respiration, and a method of generating a 3D deformation model for use in alignment.

An image alignment device of the invention includes storage means for storing a 3D deformation model of a target organ representing nonlinear 3D deformation of the inside of the target organ due to respiration, image acquisition means for acquiring a first 3D image and a second 3D image obtained by imaging a target organ of a patient in different phases of respiration, position estimation means for estimating the positions of the pixels on the second 3D image representing the same positions on the target organ as a plurality of sampled pixels in a target organ region on the first 3D image using displacement due to changes in phase of points on the 3D deformation model corresponding to the positions on the target organ represented by the pixels, and alignment means for performing non-rigid alignment between the first 3D image and the second 3D image using the estimated positions of the pixels on the second 3D image.

The alignment between the two 3D images refers to deformation of one or both of the images such that the positions of the object included in the images match each other.

In the image alignment device, the alignment means may perform the non-rigid alignment by performing a process for setting the value of at least one parameter in a process for finding corresponding pixels on the second 3D image representing the same positions on the target organ as the pixels on the first 3D image and finding the corresponding pixels using the estimated positions of the pixels on the second 3D image.

The parameters in the process for finding the corresponding pixels include, for example, the initial value of the amount of displacement allocated to each control point of the B-spline transformation function in a case of performing alignment with the B-spline transformation function, a motion vector given to each pixel in a case of performing alignment with a motion vector, a set position of each search range in a case of performing alignment by setting the search range on the second 3D image and searching for the corresponding pixel within the range, and the like.

In the image alignment device, the alignment means may deform the first 3D image such that the pixels on the first 3D image come to the estimated positions of the pixels on the second 3D image and may perform the non-rigid alignment between the first 3D image after deformation and the second 3D image.

In the image alignment device, the alignment means may perform the non-rigid alignment using a quasi-Newton method.

A method of generating a 3D deformation model of the invention which generates the 3D deformation model for use in the image alignment device includes acquiring a plurality of 3D images obtained by imaging the target organ of each of a plurality of patients in different phases of respiration, specifying pixels representing a plurality of sampled points inside the target organ in a plurality of acquired 3D images of each patient and acquiring displacement due to changes in phase of the plurality of sampled points based on shifts of the positions of the specified pixels in the plurality of 3D images, and determining displacement of the points inside the target organ due to respiration statistically using the acquired displacement to generate the 3D deformation model of the target organ.

An image alignment method of the invention which is executed by an image alignment device including storage means, image acquisition means, position estimation means, and alignment means includes causing the image acquisition means to acquire a first 3D image and a second 3D image obtained by imaging a target organ of a patient in different phases of respiration, causing the position estimation means to read a 3D deformation model of the target organ, which is stored in the storage means in advance and represents nonlinear 3D deformation of the inside of the target organ due to respiration, and to estimate the positions of the pixels on the second 3D image representing the same positions on the target organ as a plurality of sampled pixels in a target organ region on the first 3D image using displacement due to changes in phase of points on the 3D deformation model corresponding to the positions on the target organ represented by the pixels, and causing the alignment means to perform non-rigid alignment between the first 3D image and the second 3D image using the estimated positions of the pixels on the second 3D image.

An image alignment program of the invention causes a computer to function as storage means for storing a 3D deformation model of a target organ representing nonlinear 3D deformation of the inside of the target organ due to respiration, image acquisition means for acquiring a first 3D image and a second 3D image obtained by imaging a target organ of a patient in different phases of respiration, position estimation means for estimating the positions of the pixels on the second 3D image representing the same positions on the target organ as a plurality of sampled pixels in a target organ region on the first 3D image using displacement due to changes in phase of points on the 3D deformation model corresponding to the positions on the target organ represented by the pixels, and alignment means for performing non-rigid alignment between the first 3D image and the second 3D image using the estimated positions of the pixels on the second 3D image.

The image alignment program normally has a plurality of program modules, and the functions of the respective means are realized by one or a plurality of program modules. A program module group is recorded in a recording medium, such as a CD-ROM or a DVD, or is recorded in a storage attached to a server computer or a network storage in a downloadable state and provided to the user.

According to the image alignment device, method, and program of the invention, when performing alignment between the first 3D image and the second 3D image obtained by imaging the target organ of the patient in different phases of respiration, the 3D deformation model of the target organ which is generated and stored in the storage means in advance and represents nonlinear 3D deformation of the inside of the target organ due to respiration is read from the storage means. The positions of pixels on the second 3D image representing the same positions on the target organ as a plurality of sampled pixels in a target organ region on the first 3D image are estimated using displacement due to changes in phase of points on the 3D deformation model corresponding to the positions on the target organ represented by the pixels. That is, the correspondence relationship of the pixels between the first 3D image and the second 3D image is estimated with high accuracy based on the nonlinear deformation characteristics of the target organ (rough alignment), and the non-rigid alignment (local alignment) is performed between the first 3D image and the second 3D image using the estimated positions of the pixels on the second 3D image. Therefore, it is possible to perform more accurate alignment than in the method in the related art in which a linear transformation process, such as affine transformation, is performed, as the rough alignment prior to the local alignment.

DESCRIPTION OF THE PREFERRED EMBODIMENTS

Figure 1:
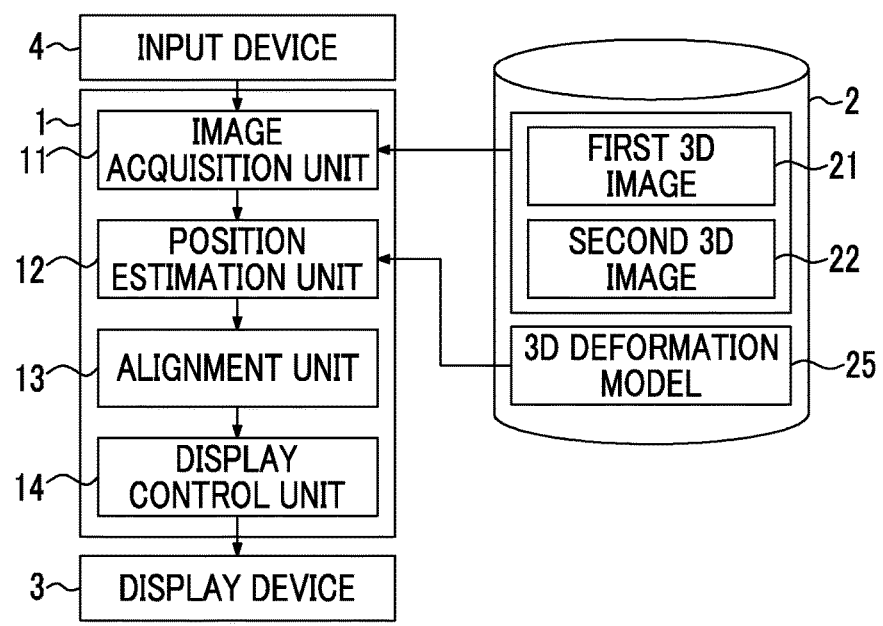
FIG. 1 is a schematic configuration diagram of an image alignment device according to an embodiment of the invention.

Hereinafter, an embodiment of an image alignment device, method, and program, and a method of generating a 3D deformation model of the invention will be described in detail referring to the drawings. Although the invention can be applied to a process for performing alignment between two 3D images obtained by imaging various target organs of a patient in arbitrary different respiratory phases, here, an example where the invention is applied to alignment of a 3D image 21 (first 3D image) at the time of inspiration obtained by imaging a lung (chest) of a target patient at a maximum inspiration level (complete inspiration) and a 3D image 22 (second 3D image) at the time of expiration obtained by imaging the lung at a maximum expiration level (complete expiration) will be described.

FIG. 1 shows the schematic configuration of an image alignment device realized by installing an image alignment program on a computer used by a physician. An image alignment device 1 includes a processor and a memory, and further includes a storage 2, such as a hard disk drive (HDD). A display device 3, such as a display, and an input device 4, such as a mouse and a keyboard, are connected to the image alignment device 1.

The image alignment program and data referred to by the program are stored in the storage 2 and loaded into the memory at starting. The image alignment program defines an image acquisition process, a position estimation process, an alignment process, and a display control process as processes executed on a CPU.

The CPU executes the respective processes described above according to the definitions of the program, whereby a computer functions as an image acquisition unit 11, a position estimation unit 12, an alignment unit 13, and a display control unit 14 described below.

A first 3D image and a second 3D image transferred from an inspection department in charge of imaging, or a first 3D image and a second 3D image acquired through a database search are stored in the storage 2. In this embodiment, a 3D image 21 (first 3D image) at the time of inspiration obtained by a lung (chest) of one target patient at a maximum inspiration level using an imaging device, such as computed tomography (CT) or a magnetic resonance imaging (MRI), and a 3D image 22 (second 3D image) at the time of expiration obtained by imaging the lung at a maximum expiration level using the imaging device are transferred from the inspection department and stored in the storage 2. Furthermore, a 3D deformation model 25 which is generated by a 3D deformation model generation method described below in advance and represents nonlinear 3D deformation of the inside of the lung due to respiration is stored in the storage 2.

Figure 2:
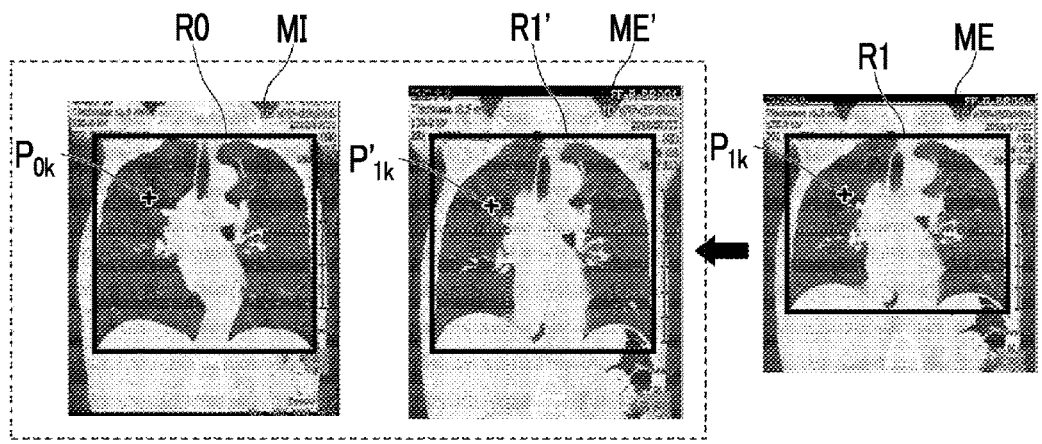
FIG. 2 is a diagram illustrating a method of generating a 3D deformation model.

The method of generating the 3D deformation model 25 of the lung will be described. First, for each of a plurality of patients (the total number N of patients) having various physiques regardless of age and sex, a 3D image MI at the time of inspiration obtained by imaging a lung (chest) at a maximum inspiration level and a 3D image ME at the time of expiration obtained by imaging the lung at a maximum expiration level are acquired. FIG. 2 shows images of the 3D image MI at the time of inspiration and the 3D image ME at the time of expiration. In FIG. 2, for ease of understanding, a 3D space region is expressed as a 2D plane.

Next, in the 3D image MI at the time of inspiration and the 3D image ME at the time of expiration of each patient (n-th patient: n=1 to N), as shown in FIG. 2, a pair $P_{0k}$ and $P_{1k}$ (k=1 to K: K is the number of landmarks in each 3D image) of points (hereinafter, referred to as landmarks) representing the same position in an anatomical structure is specified, and the landmark $P_{1k}=(x_{1k},y_{1k},z_{1k})$ on the 3D image ME at the time of expiration corresponding to the landmark $P_{0k}=(x_{0k},y_{0k},z_{0k})$ on the 3D image MI at the time of inspiration is determined. At this time, the position of each landmark can be specified automatically or based on a manual input from a user.

Next, a lung field region is extracted in the 3D image MI at the time of inspiration and the 3D image ME at the time of expiration. As an extraction method of a lung field region, a method which generates a histogram of a density value of each pixel from each piece of image data and extracts a lung field region through a through process, a method which performs a threshold process using a partial histogram and approximates the contour with a spline curve, or the like can be used.

Next, as shown in FIG. 2, sub-volumes R0 and R1 having the regions inside the positions of both ends in the respective directions of the x axis, the y axis, and the z axis of the respective extracted lung field regions in the 3D image MI at the time of inspiration and the 3D image ME at the time of expiration are determined. Then, in a case where the processes of enlargement/reduction and parallel movement are performed on the 3D image ME at the time of expiration such that the sub-volumes R0 and R1 match each other in position and size in the respective directions of the x axis, the y axis, and the z axis, a matrix $S_n=(s_x^n,s_y^n,s_z^n)$ defining enlargement/reduction in the respective directions of the x axis, the y axis, and the z axis and a matrix $T_n=(t_x^n,t_y^n,t_z^n)$ defining parallel movement in the respective directions of the x axis, the y axis, and the z axis are determined, the processes of enlargement/reduction with the matrix $S_n$ and parallel movement with the matrix $T_n$ is performed on the landmark $P_{1k}$ on the 3D image ME at the time of expiration using Expression (1) described below, and the position of a landmark $P_{1k}'$ on the 3D image ME at the time of expiration subjected to the processes of enlargement/reduction and parallel movement is calculated.

$$P_{1k}^* = S_n P_{1k} + T_n; S_n = \begin{pmatrix} s_x^n & & \\ & s_y^n & \\ & & s_z^n \end{pmatrix}; T_n = (t_x^n, t_y^n, t_z^n)^T \quad (1)$$

Next, for each of all landmark $P_{0k}$ on the 3D image MI at the time of inspiration, the shift (amount of movement) $v(P_{0k})=P_{1k}'-P_{0k}$ of the position of the landmark $P_{1k}'$ on the 3D image ME determined by the calculation based on the position of the landmark $P_{0k}$ on the 3D image MI at the time of inspiration is calculated, and a vector field $V_n(P_n)$ representing the shift (amount of movement) at an arbitrary point $P_n=(x,y,z)$ on the 3D image MI at the time of inspiration is calculated using the shifts (amount of movement) at all landmarks $P_{0k}$ by Expression (2) described below.

$$V_n P(n) = \frac{1}{w(P_n)} \sum_{k=1}^{K} V_k(P_n) \exp(-\|P_n - P_{0k}\|^2/2\sigma^2) \quad (2)$$

$$w(P_n) = \sum_{k=1}^{K} \exp(-\|P_n - P_{0k}\|^2/2\sigma^2)$$

If the calculation of the vector fields for all patients is completed, the 3D deformation model of the lung is generated statistically using the calculated vector fields. Specifically, first, in a case where a standard lung field volume (for example, 256×256×256 voxels) is defined and enlargement/reduction is performed on the 3D image MI at the time of inspiration of the patient such that the size of the determined sub-volume R0 in the 3D image MI (reference image) at the time of inspiration of each patient (n-th patient: n=1 to N) matches the size of the standard lung field volume, a matrix $S_{mn}=(s_x^{mn},s_y^{mn},s_z^{mn})$ defining enlargement/reduction in the respective directions of the x axis, the y axis, and the z axis is determined, and the vector field determined for the patient is normalized through enlargement/reduction with the matrix $S_{mn}$ by Expression (3) described below.

$$P_m = S_{mn} P_n; S_{mn} = \begin{pmatrix} s_x^{mn} & & \\ & s_y^{mn} & \\ & & s_z^{mn} \end{pmatrix}; v_n^m(P_m) = S_{mn} v_n(P_n) \quad (3)$$

Next, one vector field representing the vector fields is derived statistically using the normalized vector fields of all patients and set as the 3D deformation model 25 of the lung. As one of the simplest methods which determine one vector field representing a plurality of vector fields, as shown in Expression (4) described below, there is a method which determines the average of the normalized vector fields of all patients. In this embodiment, the thus-determined 3D deformation model 25 of the lung is stored in the storage 2 in the form of a B-spline transformation function suitable for use in non-rigid alignment.

$$v^m(P_m) = \frac{1}{N} \sum_{n=1}^{N} v_n^m(P_m) \quad (4)$$

The image acquisition unit 11 acquires the 3D image 21 (first 3D image) at the time of inspiration and the 3D image 22 (second 3D image) at the time of expiration of the target patient from the storage 2 to the memory. In this embodiment, if a predetermined alignment function is selected on a selection menu, the image alignment device 1 requests the user to select or input information necessary for specifying the first and second 3D images. Then, if the user operates the input device 4 to specify the first and second 3D images, the image acquisition unit 11 acquires the 3D image 21 at the time of inspiration and the 3D image 22 at the time of expiration from the storage 2 to the memory.

The position estimation unit 12 reads the 3D deformation model 25 of the lung, which is generated by the above-described 3D deformation model generation method and stored in the storage 2 in advance, from the storage 2, and estimates the correspondence relationship of the pixels between the 3D image 21 at the time of inspiration and the 3D image 22 at the time of expiration based on the 3D deformation model 25. Specifically, first, the lung field region is extracted in each of the 3D image 21 at the time of inspiration and the 3D image 22 at the time of expiration. As an extraction method of a lung field region, a method which generates a histogram of a density value of each pixel from each piece of image data and extracts a lung field region through a through process, a method which performs a threshold process using a partial histogram and approximates the contour with a spline curve, or the like can be used.

Next, the sub-volume having the region inside the positions of both ends in the respective directions of the x axis, the y axis, and the z axis of each extracted lung field region in each of the 3D image 21 at the time of inspiration and the 3D image 22 at the time of expiration is determined. Then, in a case where enlargement/reduction is performed on the 3D image 21 at the time of inspiration such that the size of the sub-volume determined in the 3D image 21 at the time of inspiration matches the size of the standard lung field volume, the matrix $S_{mn}=(s_x^{mn}, s_y^{mn}, s_z^{mn})$ defining enlargement/reduction in the respective directions of the x axis, the y axis, and the z axis is determined, and the scale of the vector field $v_n^m(P_m)$ of the 3D deformation model 25 of the lung is adjusted using the determined matrix $S_{mn}$ by Expression (5) described below, thereby determining the vector field $v_n(P_n)$ scaled to the 3D image 21 at the time of inspiration of the target patient.

$$v_n(P_n) = S_{nm}^{-1} v_n^m(P_m) \quad (5)$$

The vector field $v_n(P_n)$ determined by Expression (5) represents the shift (amount of movement) of an internal tissue of the lung in a state where the determined sub-volumes of the lung field regions in the 3D image 21 at the time of inspiration and the 3D image 22 at the time of expiration are aligned in the same size, and movement accompanied by a change in the size of the whole lung field region is excluded; thus, in a case where the processes of parallel enlargement/reduction and movement are performed on the 3D image 22 at the time of expiration such that the sub-volumes determined in the 3D image 21 at the time of inspiration and the 3D image 22 at the time of expiration match each other in position and size in the respective directions of the x axis, the y axis, and the z axis, the position estimation unit 12 further determines a matrix $S=(s_x, s_y, s_z)$ defining enlargement/reduction in the respective directions of the x axis, the y axis, and the z axis, and a matrix $T=(t_x, t_y, t_z)$ defining parallel movement in the respective directions of the x axis, the y axis, and the z axis, corrects the vector field $v_n(P_n)$ by Expression (6) described below, and determines a vector field $u_n(P_n)$ in which movement accompanied by the change in the size of the whole lung field region is reflected.

$$u_n(P_n) = S^{-1}(P_n + v_n(P_n) - T) - P_n \quad (6)$$

Then, the position estimation unit 12 gives displacement according to a vector defined at the same position (coordinates) of the vector field $u_n(P_n)$ determined by Expression (6) to an arbitrary pixel $P_n$ of the 3D image 21 at the time of inspiration, and estimates the position (coordinates) of the pixel after displacement as the position (coordinates) of the pixel on the 3D image 22 at the time of expiration representing the same position in the anatomical structure as the pixel $P_n$. With this, the correspondence relationship of the pixels between the 3D image 21 at the time of inspiration and the 3D image 22 at the time of expiration is estimated.

The alignment unit 13 performs non-rigid alignment between the 3D image 21 at the time of inspiration and the 3D image 22 at the time of expiration using the estimation result of the position estimation unit 12. The alignment unit 13 sets, for example, the initial value (parameter) allocated to each control point of the B-spline transformation function using the estimation result in the correspondence relationship of the pixels between the first 3D image and the second 3D image in the position estimation unit 12, deforms the 3D image 21 at the time of inspiration using the B-spline transformation function, and evaluates the similarity between the deformed 3D image 21 at the time of inspiration and the 3D image 22 at the time of expiration with an evaluation function representing the scale of the similarity between the pixel value of the deformed 3D image 21 at the time of inspiration and the corresponding pixel value of the 3D image 22 at the time of expiration while slightly changing the amount of displacement allocated to each control point of the B-spline transformation function, determines the B-spline transformation function which maximizes the evaluation value of the evaluation function, and deforms the 3D image 21 at the time of inspiration with the determined transformation function.

At this time, specifically, the setting of the initial value (parameter) of the amount of displacement allocated to each control point of the B-spline transformation function is performed by setting a value giving displacement such that each pixel of the deformed 3D image 21 at the time of inspiration and the pixel on the 3D image 22 at the time of expiration estimated by the position estimation unit 12 as corresponding to the pixel match each other in position when the 3D image 21 at the time of inspiration deformed by the B-spline transformation function and the 3D image 22 at the time of expiration are superimposed.

The display control unit 14 performs control such that the display device 3 displays the 3D image 21 at the time of inspiration after deformation generated by the alignment unit 13 and the 3D image 22 at the time of expiration for comparison. Furthermore, the display device 3 displays the acquired 3D image 21 at the time of inspiration before deformation and the 3D image 22 at the time of expiration and/or the respective images generated in the execution process of the image alignment program of this embodiment as necessary, such as the input from the user.

Figure 3:
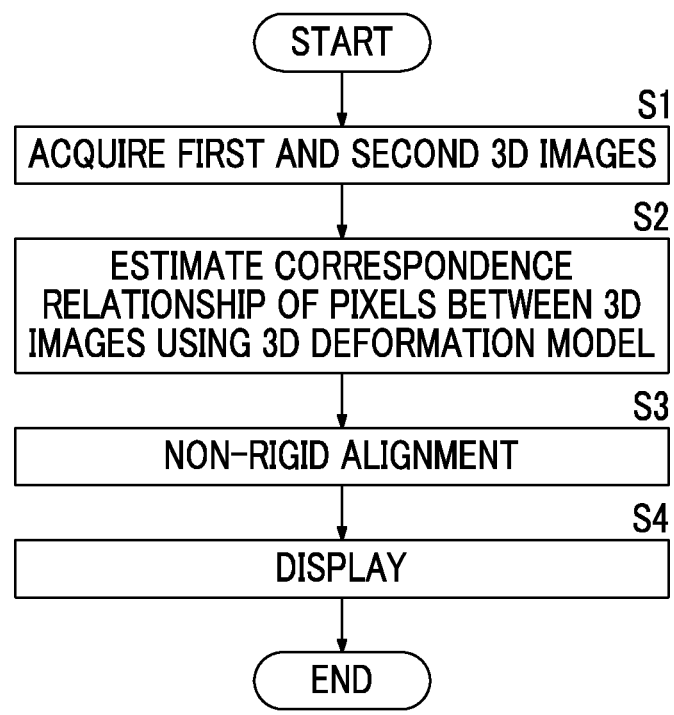
FIG. 3 is a flowchart showing the operation of the image alignment device according to the embodiment of the invention.

FIG. 3 is a flowchart showing a preferred embodiment of the image alignment method of the invention. An image alignment process of this embodiment will be described referring to FIG. 3.

First, the image acquisition unit 11 acquires the 3D image 21 (first 3D image) at the time of inspiration obtained by imaging the lung (chest) of the target patient at the maximum inspiration level and the 3D image 22 (second 3D image) at the time of expiration obtained by imaging the lung of the target patient at the maximum expiration level from the storage 2 to the memory (S1). Next, the position estimation unit 12 reads the 3D deformation model 25 of the lung generated and stored in the storage 2 in advance from the storage 2, and estimates the correspondence relationship of the pixels between the 3D image 21 at the time of inspiration and the 3D image 22 at the time of expiration based on the 3D deformation model 25 (S2). Here, first, the vector field $u_n(P_n)$ which matches the 3D deformation model 25 of the lung with image deformation from the 3D image 21 at the time of inspiration of the target patient to the 3D image 22 at the time of expiration is determined, next, displacement according to the vector defined at the same position of the determined vector field $u_n(P_n)$ is given to the arbitrary pixel $P_n$ of the 3D image 21 at the time of inspiration, and the position of the pixel after deformation is estimated as the position (coordinates) of the pixel on the 3D image 22 at the time of expiration representing the same position (coordinates) in the anatomical structure as the pixel $P_n$.

Next, the alignment unit 13 performs the non-rigid alignment between the 3D image 21 at the time of inspiration and the 3D image 22 at the time of expiration using the estimation result of the pixel position in the position estimation unit 12 (S3). At this time, the alignment unit 13 performs the non-rigid alignment by performing the process for setting the value of at least one parameter in the process (a process for determining an optimum B-spline transformation function or the like) for finding the corresponding pixel on the 3D image 22 at the time of expiration representing the same position on the lung field region as each pixel on the 3D image 21 at the time of inspiration and finding the corresponding pixel using the position of the pixel on the 3D image 22 at the time of respiration estimated in the process of Step S3. Then, the display control unit 15 performs control such that the 3D image 21 at the time of inspiration and the 3D image 22 at the time of expiration aligned with each other are displayed in parallel for comparison (S4), and the process ends.

According to the image alignment device 1 of this embodiment described above, when performing alignment between the 3D image 21 at the time of inspiration and the 3D image 22 at the time of expiration acquired by the image acquisition unit 11 and obtained by imaging the target organ of the patient in different phases of respiration, the position estimation unit 12 reads the 3D deformation model 25 of the target organ, which is generated and stored in the storage 2 in advance and represents nonlinear 3D deformation of the inside of the target organ due to respiration, from the storage 2, and estimates the correspondence relationship of the pixels between the 3D image 21 at the time of inspiration and the 3D image 22 at the time of expiration based on the 3D deformation model 25. That is, the correspondence relationship of the pixels between the 3D image 21 at the time of inspiration and the 3D image 22 at the time of expiration is estimated based on the nonlinear deformation characteristic of the target organ with high accuracy (rough alignment). The alignment unit 13 performs the non-rigid alignment (local alignment) between the 3D image 21 at the time of inspiration and the 3D image 22 at the time of expiration using the estimation result of the pixel position in the position estimation unit 12. Therefore, it is possible to perform more accurate alignment than the method in the related art in which a linear transformation process, such as affine transformation, is performed, as the rough alignment prior to the local alignment.

In the above-described embodiment, although a case where the alignment unit 13 performs the non-rigid alignment directly between the 3D image 21 at the time of inspiration and the 3D image 22 at the time of expiration by performing the process for setting the value of at least parameter in the process for finding the corresponding pixel on the 3D image 22 at the time of expiration representing the same position on the target organ as each pixel on the 3D image 21 at the time of inspiration using the position of the pixel on the 3D image 22 at the time of expiration estimated by the position estimation unit 12 and finding the corresponding pixel has been described, for example, first, the 3D image 21 at the time of inspiration may be deformed such that each pixel on the 3D image 21 at the time of inspiration comes to the estimated position of the pixel on the 3D image 22 at the time of expiration, and thereafter, the non-rigid alignment may be performed between the 3D image 21 at the time of inspiration after deformation and the 3D image 22 at the time of expiration, thereby performing the non-rigid alignment between the 3D image 21 at the time of inspiration and the 3D image 22 at the time of expiration.

What is claimed is:

1. An image alignment device comprising:
   a storage unit for storing a 3D deformation model of a target organ representing nonlinear 3D deformation of the target organ due to respiration, and which has been generated based on information about movement of the target organ due to respiration of a plurality of patients;
   an image acquisition unit for acquiring a first 3D image and a second 3D image obtained by imaging a target organ of a patient in different phases of respiration;
   a position estimation unit for estimating the positions of the pixels on the second 3D image representing the same positions on the target organ as a plurality of sampled pixels in a target organ region on the first 3D image using displacement due to changes in phase of points on the 3D deformation model corresponding to the positions on the target organ represented by the pixels; and
   an alignment unit for performing non-rigid alignment between the first 3D image and the second 3D image using the estimated positions of the pixels on the second 3D image,
   wherein the alignment unit deforms the first 3D image such that the pixels on the first 3D image come to the estimated positions of the pixels on the second 3D image and performs the non-rigid alignment between the first 3D image after deformation and the second 3D image.

2. The image alignment device according to claim 1, wherein the position estimation unit estimates the positions of the pixels on the second 3D image representing the same positions on the target organ as the plurality of sampled pixels in the target organ region on the first 3D image using a vector field that represents displacement due to changes in phase of points on the 3D deformation model corresponding to the positions on the target organ represented by the pixels.

3. The image alignment device according to claim 1, wherein the alignment unit performs the non-rigid alignment by performing a process for setting the value of at least one parameter in a process for finding corresponding pixels on the second 3D image representing the same positions on the target organ as the pixels on the first 3D image and finding the corresponding pixels using the estimated positions of the pixels on the second 3D image.

4. The image alignment device according to claim 1, wherein the alignment unit performs the non-rigid alignment using a quasi-Newton method.

5. A method of generating a 3D deformation model which the 3D deformation model for use in the image alignment device according to claim 1, the method comprising:

acquiring a plurality of 3D images obtained by imaging the target organ of each of a plurality of patients in different phases of respiration;

specifying pixels representing a plurality of sampled points inside the target organ in a plurality of acquired 3D images of each patient and acquiring a vector field that represents displacement due to changes in phase of the plurality of sampled points based on shifts of the positions of the specified pixels in the plurality of 3D images; and determining displacement of the points inside the target organ due to respiration statistically using the acquired displacement to generate the 3D deformation model of the target organ.

6. The method of claim 5, wherein the positions of the pixels on the second 3D image are estimated by adjusting the vector field by way of applying enlargement/reduction and parallel movement transforms to the vector field.

7. An image alignment device according to claim 1, wherein the position estimation unit estimates the positions of the pixels on the second 3D image by adjusting the vector field by way of applying enlargement/reduction and parallel movement transforms to the vector field.

8. An image alignment device according to claim 1, wherein the alignment unit performs the non-rigid alignment between the first 3D image, after a deformation, and the second 3D image.

9. An image alignment device according to claim 1, wherein the correspondence relationship of the pixels between the first 3D image and the second 3D image is estimated with a rough alignment of the target organ and a local alignment between the first 3D image and the second 3D image.

10. An image alignment method which is executed by an image alignment device including a storage unit, an image acquisition unit, a position estimation unit, and an alignment unit, the image alignment method comprising:

causing the image acquisition unit to acquire a first 3D image and a second 3D image obtained by imaging a target organ of a patient in different phases of respiration;

causing the position estimation unit to read a 3D deformation model of the target organ, which is stored in the storage unit in advance and represents nonlinear 3D deformation of the target organ due to respiration, and which has been generated based on information about movement of the target organ due to respiration of a plurality of patients, and to estimate the positions of the pixels on the second 3D image representing the same positions on the target organ as a plurality of sampled pixels in a target organ region on the first 3D image using a vector field that represents displacement due to changes in phase of points on the 3D deformation model corresponding to the positions on the target organ represented by the pixels; and causing the alignment unit to perform non-rigid alignment between the first 3D image and the second 3D image using the estimated positions of the pixels on the second 3D image, wherein the alignment unit deforms the first 3D image such that the pixels on the first 3D image come to the estimated positions of the pixels on the second 3D image and performs the non-rigid alignment between the first 3D image after deformation and the second 3D image.

11. The method of claim 10, wherein the positions of the pixels on the second 3D image are estimated by adjusting the vector field by way of applying enlargement/reduction and parallel movement transforms to the vector field.

12. A non-transitory computer-readable recording medium having stored therein an image alignment program which causes a computer to function as:

a storage unit for storing a 3D deformation model of a target organ representing nonlinear 3D deformation of the target organ due to respiration, and which has been generated based on information about movement of the target organ due to respiration of a plurality of patients;

an image acquisition unit for acquiring a first 3D image and a second 3D image obtained by imaging a target organ of a patient in different phases of respiration;

a position estimation unit for estimating the positions of the pixels on the second 3D image representing the same positions on the target organ as a plurality of sampled pixels in a target organ region on the first 3D image using a vector field that represents displacement due to changes in phase of points on the 3D deformation model corresponding to the positions on the target organ represented by the pixels; and an alignment unit for performing non-rigid alignment between the first 3D image and the second 3D image using the estimated positions of the pixels on the second 3D image, wherein the alignment unit deforms the first 3D image such that the pixels on the first 3D image come to the estimated position of the pixels on the second 3D image and performs the non-rigid alignment between the first 3D mage after deformation and the second 3D image.

13. The non-transitory computer-readable recording medium of claim 12, wherein the positions of the pixels on the second 3D image are estimated by adjusting the vector field by way of applying enlargement/reduction and parallel movement transforms to the vector field.

* * * * *